United States Patent [19]

Fukuta et al.

[11] Patent Number: 5,442,043
[45] Date of Patent: Aug. 15, 1995

[54] PEPTIDE CONJUGATE

[75] Inventors: Makoto Fukuta, Nara; Satoshi Iinuma, Kobe; Hiroaki Okada, Suita, all of Japan

[73] Assignee: Takeda Chemical Industries, Ltd., Osaka, Japan

[21] Appl. No.: 158,245

[22] Filed: Nov. 29, 1993

[30] Foreign Application Priority Data

Nov. 27, 1992 [JP] Japan .................................. 4-318031

[51] Int. Cl.$^6$ ..................... A61K 35/14; A61K 38/00; A61K 38/28; A61K 7/00; C07K 7/00
[52] U.S. Cl. .................................. 530/303; 530/304; 530/345; 530/399; 530/394; 530/409
[58] Field of Search ............... 530/345, 399, 394, 303, 530/304, 409

[56] References Cited

U.S. PATENT DOCUMENTS 4,801,575  1/1989  Pardridge .............................. 514/4

FOREIGN PATENT DOCUMENTS 0293071  11/1988  European Pat. Off. .
8800834   2/1988  WIPO .

OTHER PUBLICATIONS

Pardridge, W. M. (1992) Pharmacol. Toxicol. 7, 3-10 Recent Developments in Peptide Drug Delivery to the Brain.

*Primary Examiner*—Jill Warden
*Assistant Examiner*—Benet Prickril
*Attorney, Agent, or Firm*—Foley & Lardner

[57] ABSTRACT

The present invention provides a conjugate capable of passing the blood-brain barrier comprising a bioactive peptide or protein incapable of passing the blood-brain barrier and a carrier peptide which exhibits substantially no bioactivity and which is capable of passing the blood-brain barrier. The conjugate makes it possible to allow a bioactive peptide or protein incapable of passing the blood-brain barrier to easily pass the blood-brain barrier for uniform transport to the brain without any side effect of the carrier peptide.

10 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly Ile Val Glu Gln Cys Cys Thr Ser Ile Cys Ser Leu Tyr Gln Leu
 1               5                  10                      15

Glu Asn Tyr Cys Asn
              20
```

( 2 ) INFORMATION FOR SEQ ID NO:2:

( i ) SEQUENCE CHARACTERISTICS:
        ( A ) LENGTH: 22 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:2:

```
Phe Val Asn Gln His Leu Cys Gly Ser His Leu Val Glu Ala Leu Tyr
 1               5                  10                      15
Leu Val Cys Gly Glu Arg
                 20
```

PEPTIDE CONJUGATE

BACKGROUND OF THE INVENTION

The present invention relates to a drug delivery system for delivering a peptide or protein drug into the brain, more specifically a conjugate between a biologically active (hereinafter "bioactive") peptide or protein and a carrier peptide capable of transporting the peptide or protein into the brain by receptor-mediated transcytosis, by means of a receptor on the cerebral capillary endothelial cell.

By means of pores and intracellular cavities present in the capillaries of tissues such as muscles, hydrophilic drugs in the blood quickly migrate into tissue intercellular fluid via intercellular routes. However, drugs in the blood do not easily migrate from capillaries to the brain, except those of molecules smaller than about 200 daltons in molecular weight which are not ionized at physiological pH or highly soluble in fat, because the cerebral capillaries have less pores and have endothelial cells bound strongly by connective tissue. This histologic filtering mechanism, known as the blood-brain barrier (BBB), represents a hindrance in chemotherapy for cerebral disease. For example, interleukin 2 (IL-2), a cytokine produced by T-cells and playing a key role in T-cell differentiation and proliferation, has recently been suggested to proliferate oligodendrocytes, astrocytes and precursor cells thereof in the central nervous system. However, IL-2 is incapable of passing the blood-brain barrier because of its high molecular weight of 15,400; its clinical application is therefore difficult. Also, nerve growth factor (NGF), as a nerve nutrition factor, plays a key role in the survival of cholinergic nerve cells in the central nervous system, and is expected to serve as a therapeutic agent for dementia diseases such as Alzheimer's disease. However, NGF is also difficult to apply clinically because it is incapable of passing the blood-brain barrier because of its high molecular weight of about 13,000.

Various methods of drug delivery to the brain have been developed so far, including direct injection and molecular modification. As a method of molecular modification, Boda et al. attempted to increase the lipophilicity of a drug to enhance its permeation via intracellular routes (Japanese Unexamined Patent Publication No. 277662/1988; EP0293071). However, this method is limited to drugs of certain molecular weight and is difficult to apply when the subject bioactive substance is a high molecular weight peptide, especially a protein.

As another approach, there have been attempts to use chimeric peptides based on endocytosis by endogenous peptide whose receptor is present on the cerebral capillary endothelial cell, such as insulin, insulin-like growth factor (IGF) and transferrin. For example, Pardridge et al. reported on chimeric peptides capable of passing the blood-brain barrier, that were prepared by binding insulin etc. with nerve drugs (Japanese Patent PCT Publication No. 500901/1989; WO88/00834). In view of the cerebral migration rate, however, carrier peptide so such as insulin, must be administered at large doses, involving the risk of severe side effects associated with blood sugar level reduction.

Meanwhile, much research has been undertaken into the relationship between the amino acid sequence and structure of insulin and its affinity for hormone receptors.

Insulin is a polypeptide hormone of 6000 daltons comprising two short polypeptide chains, called chains A and B, bound via disulfide bonds. Chain A is a polypeptide chain of 21 amino acids, having internal disulfide crosslinkage, while chain B is a polypeptide chain of 30 amino acids. Chains A and B bind together via two disulfide crosslinkages. Although human insulin produced by genetic engineering has recently been used, porcine insulin is generally used in diabetics. Porcine insulin differs from human insulin solely in that the carboxyl-terminal Tyr in chain B ($Tyr^{B30}$) is replaced by $Ala^{B30}$. Given the fact that, in four patients with insulinemia ($Phe^{B25} \rightarrow Leu^{B25}$, Chicago; $Phe^{B24} \rightarrow Ser^{B24}$, Los Angels; $Val^{43} \rightarrow Leu^{43}$, Wakayama and Tochigi), insulin lacks hormone receptor binding capability, it is suggested that B chain C-terminal amino acids and A chain N-terminal amino acids play a key role in insulin binding with hormone receptors. Also, the components of the C-termunus of chain B, especially 25-position Phe ($Phe^{B25}$) of chain B, are associated with the bioactive potency of insulin. Nakagawa et al. obtained a synthetic insulin analogue known as (B25-30) pentapeptide deficient-[$Phe^{B25}$-$\alpha$-carboxyamide]insulin, which acts as potently as natural insulin, by removing the C-terminal pentapeptide from the chain B and amidating the carboxyl group of the resulting $Phe^{B25}$ [Journal of Biological Chemistry, Vol. 261, pp. 7332–7341 (1986)]. They also showed that insulin analogues resulting from replacement of $Phe^{B25}$ with two or three other amino acid residues, i.e., (B26-30) pentapeptide deficient-[$Tyr^{B25}$-$\alpha$-carboxyamide]insulin and $His^{B25}$ analogues, are about 2.7 to 3.0 times as potent as insulin, and that analogues resulting from (B25-30) hexapeptide deficiency, (B24-30) heptapeptide deficiency or (B23-30) octapeptide deficiency possess almost no insulin activity. Also, Pullen et al. studied the crystallographic structure of insulin, pointing out that a key to expression of insulin bioactivity is molecular geometric stabilization of the oleophilic receptor binding site, including three residues in chain A ($Gly^1$, $Tyr^1$, $Asn^{21}$) and five residues in chain B ($Val^{12}$, $Tyr^{16}$, $Phe^{24}$, $Phe^{25}$, $Tyr^{26}$) [Nature, Vol. 259, pp. 369–373 (1976)].

These studies have provided a great deal of information on insulin analogues showing blood sugar reducing action and affinity for hormone receptors, but there is no report of receptors on cerebral capillaries.

In allowing a bioactive peptide or protein to pass the blood-brain barrier to transport it into the brain, it is desirable to transport the peptide or protein uniformly into the brain with minimum side effects. However, there is no well-established mode for a transport of bioactive peptide or protein meeting these requirements.

DETAILED DESCRIPTION OF THE INVENTION

Figure 1:
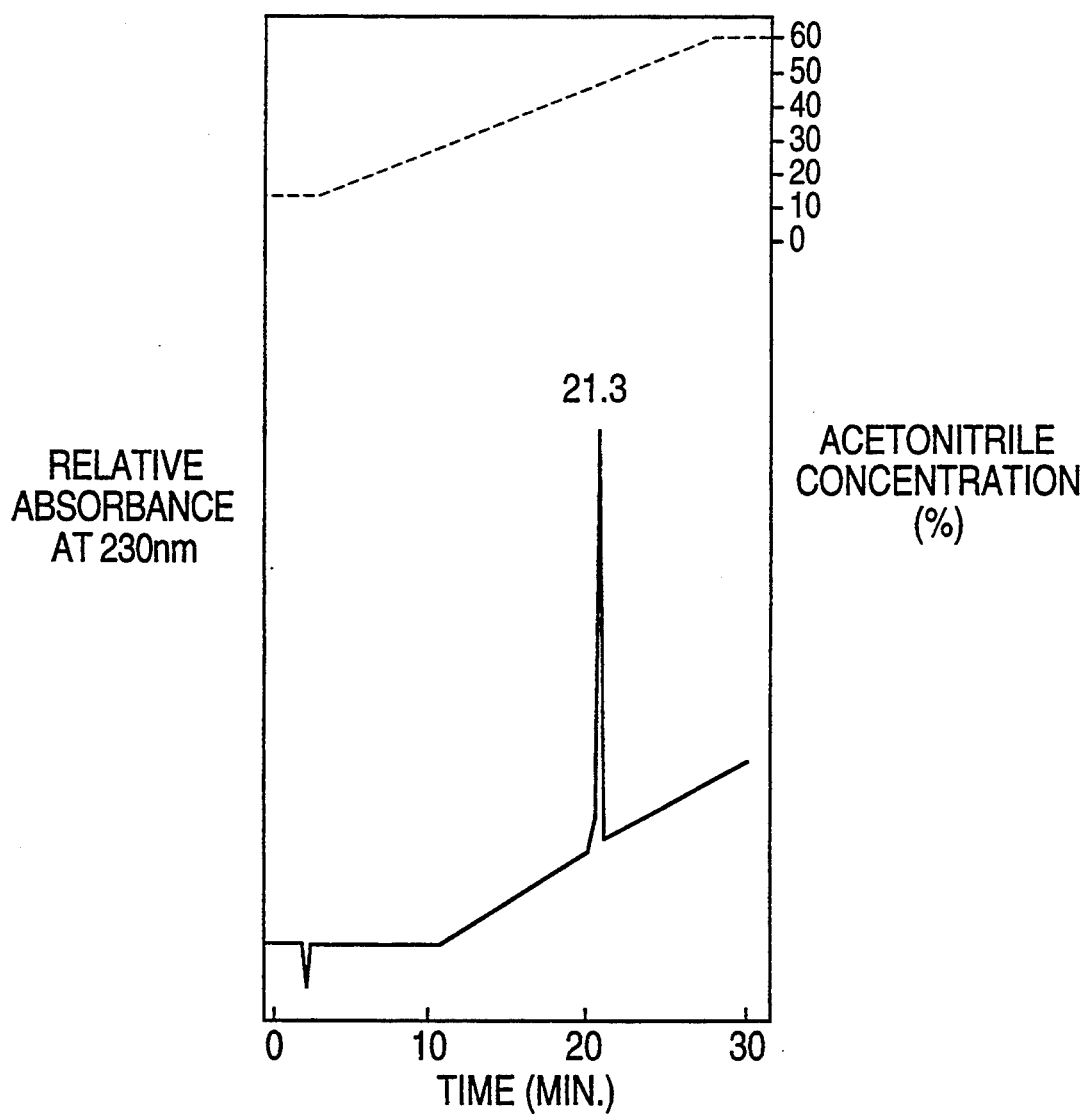
FIG. 1 is a reverse phase HPLC chromatogram of insulin fragment F001 obtained in Example 1.

Against this technical background, the present inventors sought a carrier peptide capable of passing the blood-brain barrier and showing no side effects in transporting a bioactive peptide or protein into the brain, and found that an insulin fragment, showing affinity for the insulin receptor on the cerebral capillary endothelial cell, and being less effective than insulin in blood sugar reduction, is capable of passing the blood-brain barrier by receptor-mediated transcytosis and serving as a carrier for the bioactive peptide or protein. The inventors made further investigations based on this finding to develop a carrier peptide capable of transporting a peptide or protein otherwise incapable of passing the blood-brain barrier via the physiological process of receptor-mediated transcytosis at the blood-brain barrier and capable of preventing adverse side effects associated with the activity of the carrier peptide itself, and a mode of its transport, and developed the present invention.

Accordingly, the present invention provides a peptide conjugate capable of passing the blood-brain barrier, comprising a bioactive peptide or protein normally incapable of passing the blood-brain barrier and a carrier peptide which exhibits substantially no biological activity and which is capable of passing the blood-brain barrier. In a preferred embodiment, the carrier peptide is an inert fragment of a biopeptide capable of passing the blood-brain barrier by receptor-mediated transcytosis. Preferably, the carrier peptide has a molecular weight range of 5,000 to 100,000 daltons.

More specifically, the present invention provides a conjugate as above wherein the carrier peptide is an inherent fragment of biopeptide or protein selected from the group consisting of insulin, transferrin or insulin-like growth factor I or II. Preferably, the carrier peptide is an insulin fragment comprising a peptide chain having 14 to 21 amino acid residues from the N-terminus of insulin chain A (SEQ ID No. 1) and another peptide chain having 16 to 22 amino acid residues from the N-terminus of insulin chain B (SEQ ID No. 2).

The conjugate of the present invention is useful in transporting various bioactive peptides or proteins to the brain. In particular, it is ideal for the transport of high molecular weight protein drugs, which are otherwise substantially non transportable across the blood-brain barrier.

Examples of the bioactive peptide or protein drugs to be transported across the blood-brain barrier include various nerve nutrition factors and neuropeptides which are incapable of passing the blood-brain barrier and which are useful therapeutic agents for cerebral disease. Nerve nutrition factors include those of the neurotrophine family such as nerve growth factor (NGF), brain-derived neurotrophine factor (BDNF), neurotrophine 3 (NT-3), neurotrophine 4 (NT-4), neurotrophine 5 (NT-5) and ciliary neurotrophic factor (CNTF); activin; growth factors which function in the central nervous system as well, such as basic fibroblast growth factor (bFGF), acidic fibroblast growth factor (aFGF) and epithelial growth factor (EGF); cytokines which act directly or indirectly on the nervous system or are involved in gliacyte proliferation, differentiation and activation to exhibit nerve nutrition factor action, such as interferon $\alpha$, interferon $\beta$, interferon $\gamma$, interleukin 1 (IL-1), interleukin 2 (IL-2), interleukin 3 (IL-3), interleukin 4 (IL-4), interleukin 5 (IL-5), interleukin 6 (IL-6), TNF, granulocyte macrophage colony stimulating factor (GM-CSF), granulocyte colony stimulating factor (G-CSF), macrophage colony stimulating factor (M-CSF), platelet-derived growth factor (PDGF); brain-acting hormones and neurotransmitters such as somatostatin, oxytocin, vasopressin, guaranine, VIP, adrenocorticotropic hormone (ACTH), cholecystokinin (CCK), substance-P, bombesin, motilin, glicentin, glucagon, glucagon-like peptide (GLP-1); and neuropeptides and derivatives thereof such as peptide YY (PYY) neuropeptide Y (NPY), pancreatic polypeptide (PP), neurokinin A, neurokinin B, endorphin, enkephalin, neurotensin, neuromedin K, neuromedin L, calcitonin related peptide (CGRP), endothelin, ANP ("actrial natriuretic peptide"), BNP ("brain natriuretic peptide"), CNP (C-type natriuretic peptide"), and PACAP ("pituitary adenylate cyclase activating peptide").

Enzymes such as horse radish peroxidase (HRP) are also used as a bioactive peptide in the prerent invention.

As stated above, the bioactive peptide or protein to be transported in the present invention is generally a polypeptide having a molecular weight of not lower than 200 daltons that is substantially incapable of passing the blood-brain barrier because of its hydrophilicity. It may be of natural origin derived from an animal or plant, or may be obtained by a known peptide synthesis method or genetic engineering technique. The above-described active derivatives include optical isomers, active fragments and muteins. Here, such muteins include those resulting from amino acid sequence mutation in the original protein by amino acid addition, deletion of some constituent amino acids or replacement with other amino acid such that the bioactivity of the original protein retained. The mutein may involve two or more mutations of addition, deletion and substitution.

Muteins resulting from amino acid addition include those to which at least one amino acid has been added. However, the amino acids added to the mutein do not include methionine or signal peptides from the initiation codon used to express the peptide. The amino acids added (at least one) may be of any number, as long as the essential bioactivity is retained. Muteins resulting from deletion of constituent amino acids include those resulting from deletion of at least one constituent amino acid. Any number of constituent amino acids may be deleted, as long as the essential bioactivity is retained. Muteins resulting from replacement with other amino acids include those resulting from replacement of at least one constituent amino acid by another amino acid. Any number of constituent amino acids may be replaced as long as the essential bioactivity is retained.

In the present specification, "to pass the blood-brain barrier" means that in administering a bioactive peptide or protein within the range of its ordinary acceptable dosage, the degree of blood-brain barrier permeability is such that the essential bioactivity of the peptide or protein offers bioactivity, such as a therapeutic effect on cerebral disease in the subject. For this reason, bioactive peptides or proteins showing very low blood-brain barrier permeability and derivatives thereof also fall in the category of bioactive peptides or proteins incapable of passing the blood-brain barrier as mentioned above in the present invention.

The molecular weight of the bioactive peptide or protein, such as a therapeutic agent for cerebral disease, which can be transported by the conjugate of the present invention, varies to some extent depending on the molecule's steric morphology, size, stability to enzyme, water solubility and other factors. Although any low molecular weight peptides could be used as the bioactive peptide, a bioactive protein suitable for transport according to the present invention generally has a molecular weight of not lower than about 200 daltons and not higher than about 120,000 daltons. The transport capability of the conjugate is enhanced in the case of peptide or protein drugs whose molecular weight is about 400 to about 80,000 daltons, preferably about 500 to about 60,000 daltons.

The carrier peptide of the present invention may be a peptide which exhibits substantially no bioactivity and which preferably shows affinity for the cerebral capillary endothelial cell. Although a peptide having affinity for a receptor on the cell is particularly preferable, any peptide capable of passing the blood-brain barrier can be used, as long as forms a conjugate with a bioactive peptide or protein which can passes the blood-brain barrier. The molecular weight of the carrier peptide is about 5,000 to about 100,000 daltons.

"A peptide which exhibits substantially no bioactivity" mentioned herein is a peptide which causes no physiological phenomena in vivo at ordinary acceptable dosages or whose resulting physiological phenomena fall within the background of physiological change. The carrier peptide of the present invention may therefore possess activity not directly associated with bioactivities such as membrane permeability and receptor affinity, preferably possessing receptor-mediated transcytotic activity on the cerebral capillary endothelial cell.

Also, from the viewpoint of antigenicity, safety etc., the carrier peptide is preferably a peptide originating from a mammal, with greater preference given to a peptide of the subject animal. It is particularly preferable to use an inert fragment of a peptide capable of passing the blood-brain barrier or a derivative thereof whose essential bioactivity has been weakened or eliminated while retaining its capability of passing the blood-brain barrier.

The carrier peptide of the present invention is exemplified by inert peptide fragments such as those of insulin, transferrin, insulin-like growth factor I (IGF-I) and insulin-like growth factor II (IGF-II), and peptides obtained from a combination of parts of their amino acid sequences and showing affinity for the cerebral capillary endothelial cell. These peptide fragments are obtainable in various ways, e.g., by decomposing insulin, etc. with proteases such as trypsin, chymotrypsin, pepsin, papain and V8 protease.

Figure 6:
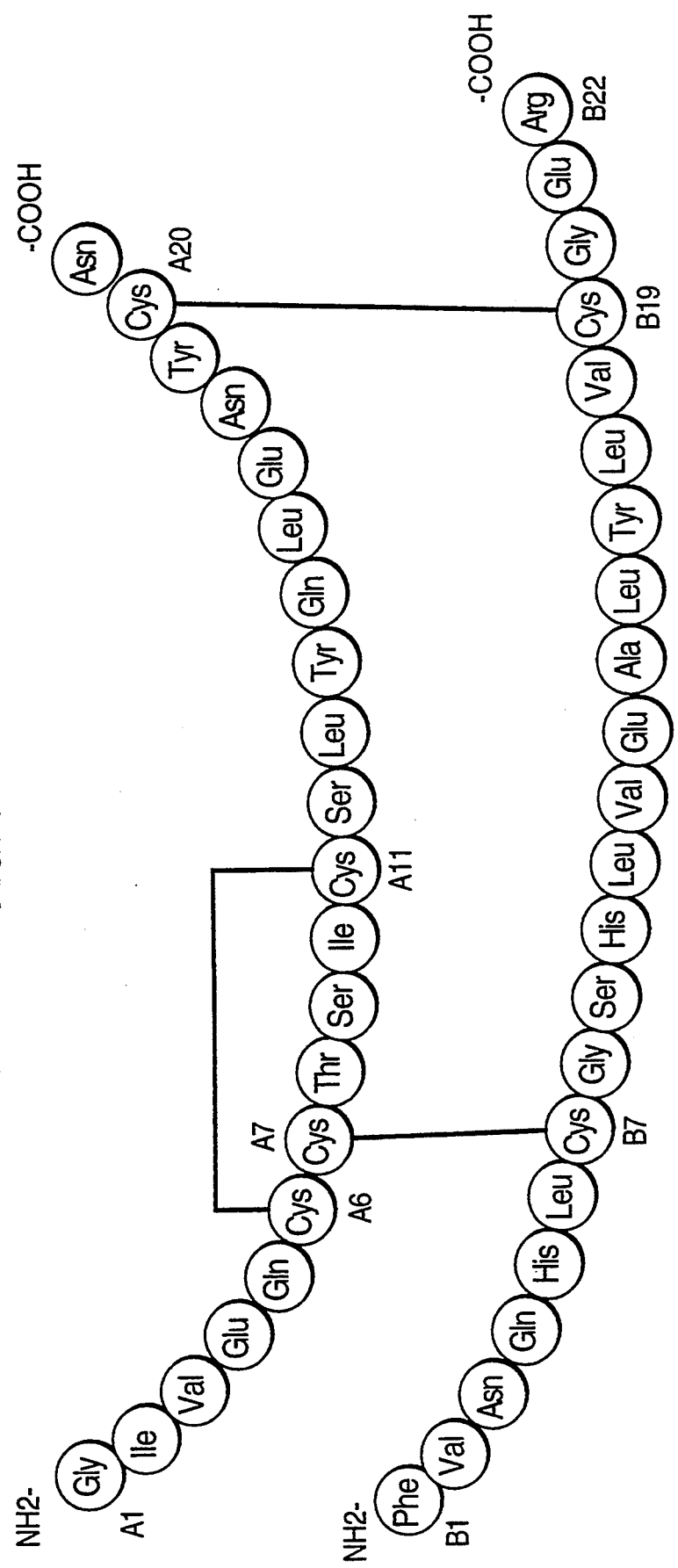
FIG. 6 is the estimated structural formula of insulin fragment F007 obtained in Example 2. (SEQ. ID NOS 1 and 2 are shown in this Figure.)

An insulin fragment used as a carrier peptide is preferably a fragment comprising a peptide chain having 14 to 21 amino acid residues from the N-terminus of chain A and another peptide chain having 16 to 22 amino acid residues from the N-terminus of chain B. To maintain binding affintly for the carebral capillary endothelial cellulor, the fragment preferably has disulfide crosinkage at the same position of between natural molecule, such as internal disulfide crosslinkage between 6th and 11th position counting from the N-terminus of chain A and two disulfide cross linkages between chain A and chain B. In particular, the (B 23–30) octapeptide-deficient insulin fragment obtained in Example 2 below (FIG. 6, SEQ ID NOS. 1 and 2), is equivalent to insulin in affinity for the receptor on the cerebral capillary endothelial cell, a fact not expected from findings concerning the affinity of conventional insulin analogues for hormone receptors, is as an example of a carrier peptide for the present invention.

Such carrier peptides can also be obtained by known peptide synthesis technologies, including the solid phase synthesis method with polystyrene resin as a carrier. This method is based on the principle that carboxyl-terminal amino acid residues are covalently bound to a resin carrier, followed by cycles of removal of the α-amino group protecting and amino acid protection, in that order, to extend the peptide toward the amino terminus to obtain a protected peptide resin having the desired amino acid sequence. When the carrier peptide comprises two or more peptide chains, for example, in the case of an insulin fragment (two chains), the two peptide chains, previously separately synthesized, may be reacted under weakly alkaline conditions to easily form disulfide bonds to yield the desired carrier peptide as a crude product which may be purified by known means of peptide or protein purification. Such known methods include gel filtration, ion exchange chromatography, hydrophobic chromatography, partition adsorption chromatography and high performance liquid chromatography.

The carrier peptide can also be obtained by methods based on genetic engineering using microbes such as bacteria and fungi or animal cells, such as hamster ovarian cells, as hosts.

The conjugate of the present invention is prepared by binding a bioactive peptide or protein to a carrier peptide by a known chemical or gene engineering technique. Specifically, chemical binding is achieved using a crosslinking agent for peptide bond formation capable of reacting with both peptide molecules (i.e., bioactive peptide or protein and carrier peptide) such as 1-ethyl-3-(3-dimethylaminopropyl)carbodiimide (EDAC, WSC). Preference is given to the method based on peptide thiolation characterized by treatment with a reagent capable of forming disulfide bonds between two peptides, such as N-succinimidyl-3-(2-pyridylthio)propionate (SPDP) or cystamine. With respect to other known binders, any one can be used, as long as it is capable of binding two peptide molecules without degrading the carrier peptide's capability of passing the blood-brain barrier or the bioactive peptide's or protein's bioactivity due to denaturation. More specifically, on the basis of reactivity to functional groups and spacer length, the following crosslinking agents, for instance, are chosen: glutaraldehyde, 4,4'-diisothiocyanostylbene-2,2'-disulfonic acid (DIDS), N-(E-maleimidocaproyloxy)succinimide (EMCS), N-(gamma-maleimidobutyloxy)-succinimide (GMBS), dithiobis(succinimidylpropionate) (DSP) and 4,4'-dithiobisphenylazide (DTBPA) as an optical activator.

These conjugates can also be synthesized by forming amide bonds by the ordinary liquid phase method or solid phase method, or by forming disulfide bonds using reducing agents.

It is also possible to directly express these bioactive peptide conjugates by known genetic engineering techniques using microbes such as bacteria and fungi or animal cells such as hamster ovarian cells. Specifically, this can be accomplished by (1) deriving a cDNA corresponding to the carrier peptide from a known cDNA encoding a peptide capable of passing the B.B.B such as insulin, (2) directly binding a cDNA encoding the bioactive peptide or protein to be transported directly to the cDNA encoding the carrier peptide, and (3) transforming an appropriate host cell with a vector containing said cDNA.

With respect to the conjugate, the binding ratio of the bioactive peptide or protein and the carrier peptide can be chosen according to the carrier's transporting capability, drug activity, recovery to active substance etc. This molar ratio of carrier to bioactive peptide or protein drug is 4:1 to 1:5, preferably 2::1 to 1:3.

In the present invention, the ratio of the bioactive peptide or protein for a drug and the carrier peptide is variable depending on the combination of both peptides used, i.e., on the kind and number of functional groups involved in the protein binding reaction in each peptide chain, such as N-terminal or C-terminal basic amino acids (e.g., arginine, lysine, histidine), acidic amino acids (e.g., glutamic acid, aspartic acid) and cysteine residues. It can also be adjusted by controlling reaction conditions such as kinds and concentrations of reagents and reaction time.

The thus-obtained conjugate, prepared singly or in combination, can be administered to warm-blooded animals, particularly mammals (e.g., bovines, horses, dogs, cats, humans) to prevent and/or treat various cerebral diseases such as brain tumor, cerebral vascular disorder and Alzheimer's disease. It can also be administered safely in combination with other pharmacologically acceptable drugs.

The conjugate is preferably administered parenterally, e.g., intravascularly, intramuscularly or subcutaneously, in the form of an injection, with preference given to intravenous or intra-arterial administration. In preparing an injection of the conjugate of the present invention, antiseptics, stabilizers, isotonizing agents and other additives commonly used in injections may be added.

For example, an injection in an aqueous solution, oil solution or suspension is prepared by a conventional method using a solvent such as distilled water for injection, an aqueous solvent (physiological saline, Ringer's solution) or an oily solvent (e.g., sesame oil, olive oil) and, where necessary, additives such as a dissolution aid (e.g., Tween-80, arginine), buffers (e.g., sodium phosphate, sodium citrate, sodium acetate), isotonizing agents (e.g., glucose, glycerol, sorbitol), stabilizers (e.g., human serum albumin, polyethylene glycol), preservatives (e.g., benzyl alcohol, phenol) and soothing agents (e.g., benzalkonium chloride, procaine hydrochloride).

Also, a solid injectable preparation to be dissolved or dispersed freshly before use can be prepared by a conventional method by mixing a solvent, a dispersant (e.g., distilled water, physiological saline, glucose solution), an excipient (e.g., carboxymethyl cellulose (CMC), mannitol, sodium alginate), a preservative (e.g., benzyl alcohol, benzalkonium chloride, phenol) and a soothing agent (e.g., glucose, calcium gluconate, procaine hydrochloride).

Non-injection preparations include those for administration to nasal, oral, rectal, vaginal, uterine and other mucosa, sustained-release microcapsular preparations and controlled-release preparations such as implant preparations. In preparing these preparations, monosaccharides such as glucose, amino acids, various salts, human serum albumin etc. may be added. Ordinary isotonizing agents as described above may also be added, as can pH regulators, soothing agents, antiseptics, and known absorption promoters (e.g., citric acid, α-cyclodextrin, mandelic acid, sodium salicylate, bile acid, polyoxyethylene-(9)-lauryl ether, taurodihydrofusidilic acid) to prepare a safe, effective conjugate preparation.

The conjugate of the present invention is expected to have a sufficient effect at relatively low dosage in suppressing or treating Alzheimer's disease when used to administer human NGF, BDNF, NT, FGF etc., which are nerve nutrition factors. Also, for various brain-acting neuropeptides such as enkephalin, somatostatin, substance-P and VIP, dose reduction and peripheral side effect reduction are expected as a result of efficient delivery to the brain.

The dosage of the conjugate of the present invention in humans varies depending on type of bioactive peptide or protein used, subject of administration, symptoms, dosage form etc., but it may be of any level, as long as the desired pharmacologic effect is obtained; normally it is parenterally administered at about 10 μg to about 2 g, preferably about 20 μg to about 1 g, daily in one to three portions.

A protein conjugate of the present invention may be also used for detecting safely the receptors such as insulin, transferrin, insulin-like growth factor I or II, on the several organs, such as liver, kidney or tumors, as well as on the endothelial cells of the brain capillary. For example, conjugates comprising a bioactive marker protein such as an enzyene (e.g. horse radish peroxidase) and carrier peptide may be used for the above purpose in combination with their specific monoclonal antibodies.

Thus the peptide conjugate, for example, the conjugat of inert insulin fragment and the marker protein may be useful for elucidation of biological effects of insulin on normal hepatocytes, lymphocytes, adipocytes, astrocytes, neurocytes or gliacytes and be available in their insulin receptor disorder. It can be also useful for detecting insulin receptor deficiency in genetic and acquired obesity, and for determining insulin dependency of tumor may cells, such as hepatoma or breast cancer.

Abbreviations for bases, amino acids etc. used in the present specification and drawings attached thereto are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated.

DNA: Deoxyribonucleic acid
A: Adenine
T: Thymine
G: Guanine
C: Cytosine
Gly: Glycine (G)
Ala: Alanine (A)
Val: Valine (V)
Leu: Leucine (L)
Ile: Isoleucine (I)
Ser: Serine (S)
Thr: Threonine (T)
Cys: Cysteine (C)
½Cys: Half cystine
Met: Methionine (M)

Glu: Glutamic acid (E)
Asp: Aspartic acid (D)
Lys: Lysine (K)
Arg: Arginine (R)
His: Histidine (H)
Phe: Phenylalanine (F)
Tyr: Tyrosine (Y)
Trp: Tryptophan (W)
Pro: Proline (P)
Asn: Asparagine (N)
Gln: Glutamine (Q)

EXAMPLES

The present invention is hereinafter described in more detail by means of the following Preparation Example, Reference Examples and Working Examples, which are not to be construed as limitative to the present invention.

Reference Example 1: Blood-Brain Barrier Permeable Test

A $^{125}$I-labeled sample-carrier peptide conjugate was dissolved in physiological saline and intravenously administered to ICR mice. After a given period of time, $^{125}$I-labeled sample incorporation in the brain was determined. By comparing cerebral incorporation of the $^{125}$I-labeled sample in the conjugate with that of a similarly prepared $^{125}$I-labeled sample alone at each time point, the in vivo transport capability of the carrier peptide was assessed.

Example 1: Preparation and Identification of F001

Figure 2:
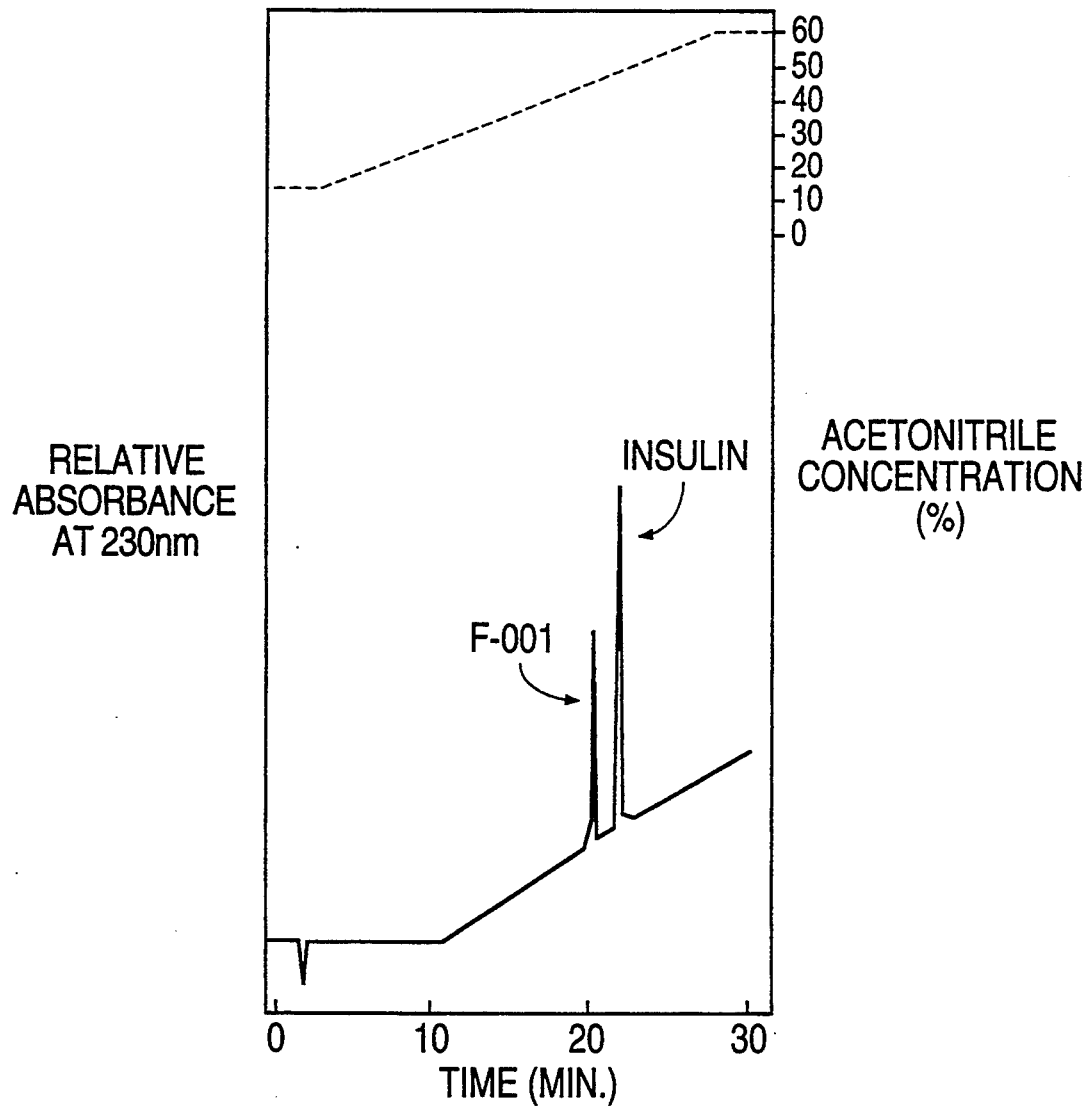
FIG. 2 is a reverse phase HPLC chromatogram of insulin fragment F001 obtained in Example 1 and insulin (whole molecule).
Figure 3:
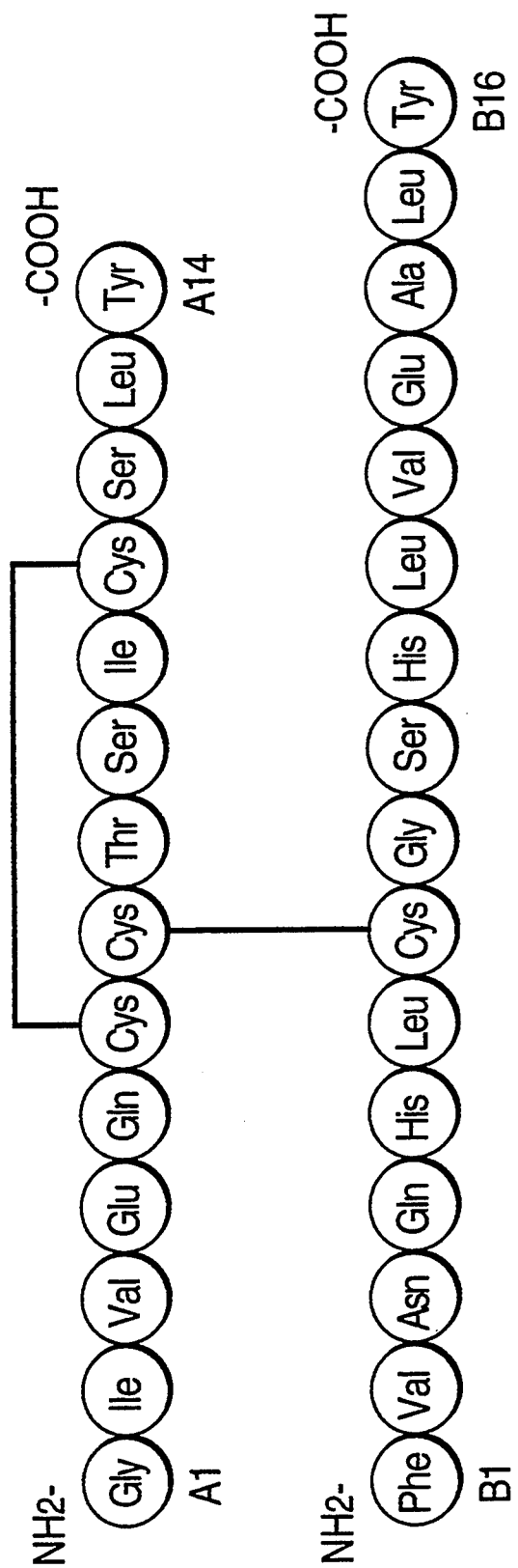
FIG. 3 is the estimated structural formula of insulin fragment F001 obtained in Example 1. (Residues 1–14 of SEQ ID NO:1 and residues 1–16 of SEQ ID NO:2 are shown in this Figure.)

100 mg of porcine insulin (Shimizu Seiyaku), dissolved in 2.5 ml of 10 mM hydrochloric acid, was diluted with 50 ml of 0.1M phosphate buffer (pH 7.0). To this dilution was added 5 mg of trypsin (SIGMA); the mixture kept standing at room temperature for 3 days, followed by lyophilization of the entire quantity. The resulting decomposed mixture was dissolved in 1N acetic acid, and the solution filtered through a 0.45 μm filter to remove insoluble substances. The filtrate was subjected to reverse phase preparative high performance liquid chromatography (HPLC) (column: TSK gel ODS-120T, 2.15×30 cm; flow rate 0.7 ml/min; eluted at 10% acetonitrile concentration for the first 3 minutes and then on a density gradient from 10% to 60% over the following 25 minutes) with acetonitrile/water containing 0.1% trifluoroacetic acid (TFA) as eluent. The main peak was collected and lyophilized to yield a white powder. The thus-obtained insulin fragment was named F001. F001 appeared as a single peak separated from insulin in reverse phase analytical HPLC (FIGS. 1 and 2), the yield being 6.5%. F001 was analyzed using an amino acid sequencer. From the analytical results, F001 was determined to have the structural formula shown in FIG. 3 (residues 1-14 of SEQ ID NO:1 and residues 1-16 of SEQ ID NO:2).

Example 2: Preparation and Identification of F007

Figure 4:
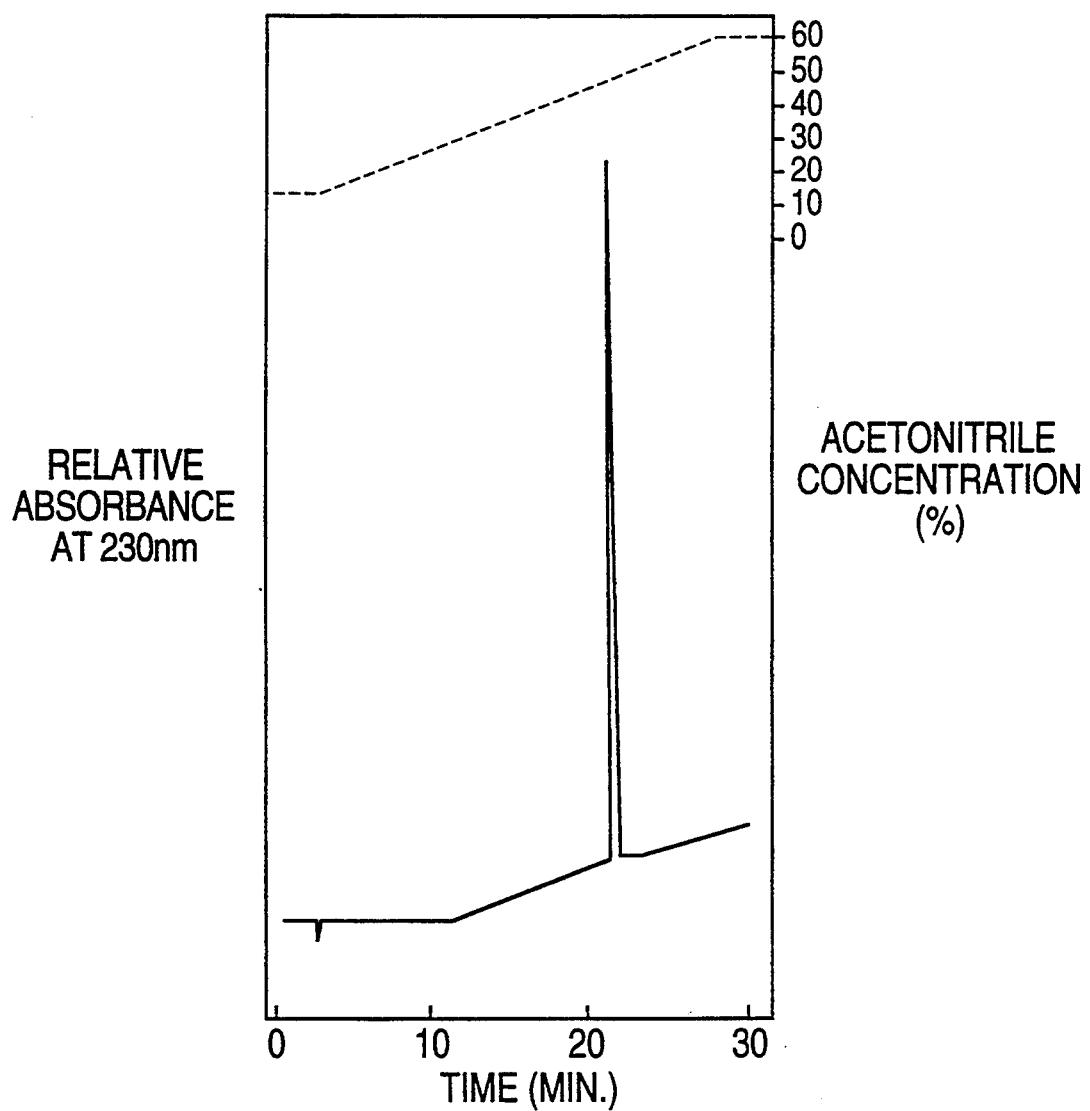
FIG. 4 is a reverse phase HPLC chromatogram of insulin fragment F007 obtained in Example 2.
Figure 5:
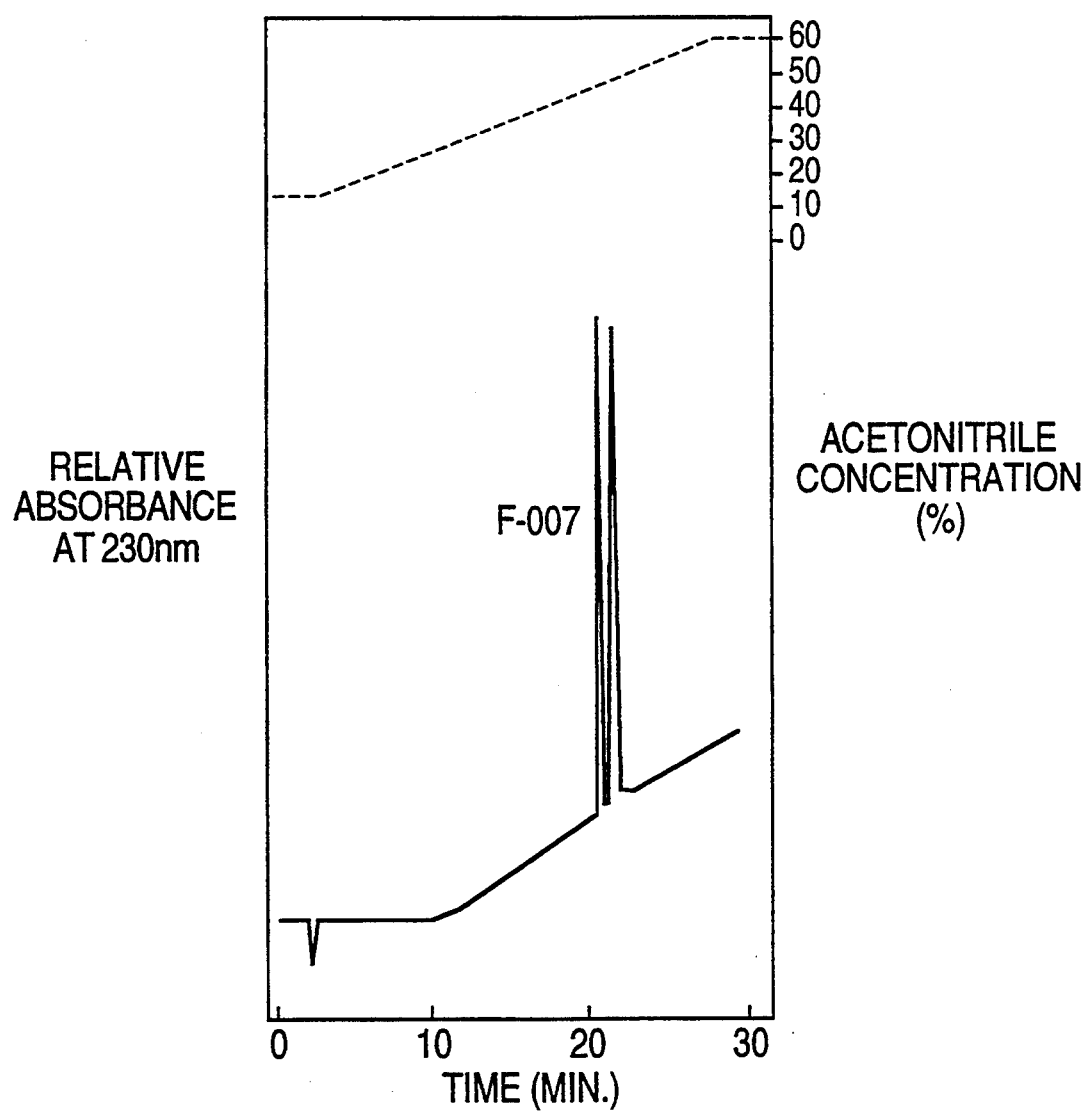
FIG. 5 is a reverse phase HPLC chromatogram of insulin fragment F007 obtained in Example 2 and insulin (whole molecule).

300 mg of porcine insulin, dissolved in 2.5 ml of 10 mM hydrochloric acid, was diluted with 150 ml of 0.1M N-ethylmorpholine (pH 8.0) containing 2 mM EDTA. To this dilution was added a solution of 45 mg of trypsin in 150 ml of 0.1M N-ethylmorpholine containing 20 mM calcium chloride, followed by incubation at 37° C. for 90 minutes. After 10 ml of 1N acetic acid was added to terminate the reaction, the entire quantity was lyophilized. The resulting decomposed mixture was dissolved in 1N acetic acid, and the solution filtered through a 0.45 μm filter to remove insoluble substances. The filtrate was subjected to reverse phase preparative HPLC (column: TSK gel ODS-120T, 2.15×30 cm; flow rate 0.7 ml/min; eluted at 10% acetonitrile concentration for the first 3 minutes and then on a density gradient from 10% to 60% over the following 25 minutes) with acetonitrile/water containing 0.1% TFA as eluent. The main peak was collected and lyophilized to yield a white powder. The thus-obtained insulin fragment was named F007. F007 appeared as a single peak separated from insulin in reverse phase analytical HPLC (FIGS. 4 and 5), the yield being 29.5%. After hydrolysis with 6N hydrochloric acid, F007 was analyzed for amino acid composition. From the analytical results (Table 1), combined with the structural formula of insulin, F007 was determined to have the structural formula shown in FIG. 6(SEQ ID NOS. 1 and 2).

TABLE 1

| | Amino Acid Analysis of F007 | | | |
|---|---|---|---|---|
| | Insulin | | F007 | |
| Amino acid | Results | Theoretical Value | Results | Theoretical Value |
| Asp | 2.9 | 3 | 2.9 | 3 |
| Glu | 6.7 | 7 | 6.3 | 7 |
| Ser | 2.8 | 3 | 3 | 3 |
| Gly | 4.2 | 4 | 3.5 | 3 |
| His | 1.9 | 2 | 1.9 | 2 |
| Arg | 1.1 | 1 | 1 | 1 |
| Thr | 1.9 | 2 | 1.1 | 1 |
| Ala | 2.1 | 2 | 1.2 | 1 |
| Pro | 1.1 | 1 | 0.2 | 0 |
| Tyr | 4.1 | 4 | 3.3 | 3 |
| Val | 3.5 | 4 | 3.6 | 4 |
| Cys | 2.5 | 6 | 2.6 | 6 |
| Ile | 1.6 | 2 | 1.7 | 2 |
| Leu | 6 | 6 | 6 | 6 |
| Phe | 3.1 | 3 | 1.5 | 1 |
| Lys | 1.1 | 1 | 0.2 | 0 |

Example 3: Receptor Affinities (1) of Insulin Fragments

In accordance with the description by Ronald T. Borchart et al. of the United States in "Characteristics of the Large Neutral Amino Acid Transport System of Bovine Brain Microvessel Endothelial Cell Monolayers" [Journal of Neurochemistry, Vol. 47, pp. 484–488 (1986)], bovine brain microvessel endothelial cells were separated in a monolayer, whose affinity for the receptor on the endothelial cell was determined. Specifically, to cultured cells reaching the stage of packed structure, each of the insulin fragments (F001 and F007) obtained in the presence of $^{125}$I-insulin in Examples 1 and 2 and non-labeled insulin was added, and affinity for the insulin receptor on the capillary endothelial cell was assessed by competitive inhibition for $^{125}$I-insulin.

As seen in Table 2, both F001 and F007 showed affinity, F007 being equivalent to the whole insulin molecule in affinity. As shown by past research, affinity for cultured cerebral capillaries serves as a good index of cerebral capillary permeability in vivo; the present example well suggests drug delivery to the brain by transcytosis via the insulin receptor.

TABLE 2

Comparison of Affinities of F001 and F007 for Receptor on the Cerebral Capillary Endothelial Cell
$^{125}$I-insulin binding ratio (%) after addition of non-labeled compound

| Addition Concentration (μM) | Insulin | F001 | F007 |
|---|---|---|---|
| 1.6 × 10² | | 13.6 ± 0.2 | |
| 1.0 × 10² | | 61.6 ± 1.2 | 11.8 ± 2.5 |

TABLE 2-continued

Comparison of Affinities of F001 and F007 for Receptor on the Cerebral Capillary Endothelial Cell $^{125}$I-insulin binding ratio (%) after addition of non-labeled compound

| Addition Concentration (μM) | Insulin | F001 | F007 |
|---|---|---|---|
| $1.0 \times 10^2$ | 23.0 ± 6.3 | 78.5 ± 3.8 | 18.1 ± 2.6 |
| $1.0 \times 10$ | 24.2 ± 1.5 | 93.2 ± 0.4 | 33.5 ± 1.7 |
| $1.0 \times 10^{-1}$ | 30.2 ± 3.9 | | 55.7 ± 6.6 |
| $1.0 \times 10^{-2}$ | 44.6 ± 0.9 | | 73.7 ± 8.8 |
| $1.0 \times 10^{-3}$ | 73.7 ± 8.3 | | 90.3 ± 2.8 |
| $1.0 \times 10^{-4}$ | 85.7 ± 8.5 | | 94.7 ± 10.8 |

Example 4: Synthesis of F007

Chains A(SEQ ID NO:1) and B(SEQ ID NO:2) of F007 were synthesized by the solid phase synthesis method with polystyrene resin as a carrier. A t-butoxycarbonyl (tBOC) group and a protecting group of the benzyl type were used for the N(α)-amino group and the amino acid side chain functional group, respectively. The cysteine residues involved in the disulfide bonds in chains A and B of F007 (7- and 20-positions in chain A and 7- and 19-positions in chain B) were protected by the maximum protection method with an acetoamidomethyl (Acm) group as a protecting group. Starting with polystyrene resin bound with C-terminal amino acids, tBOC groups were sequentially removed with 0.5% methanesulfonic acid, followed by washing with 2% pyridine. Subsequently, tBOC-protected amino acids were condensed by activation with benzotriazol-1-yl-oxy-tris(dimethylamino)-phosphonium hexafluorophosphate. After completion of the entire course of condensation, the protected peptide resin was dried under reduced pressure.

The dry protected peptide resin was stirred in hydrogen fluoride in the presence of an appropriate cation scavenger for 2 hours while ice cooling, to split off the peptide from the resin and remove the protecting groups. After the hydrogen fluoride was distilled off under reduced pressure, ether was added to the residue to precipitate the peptide. The precipitated peptide was washed with ether three times to thoroughly remove the hydrogen fluoride and scavenger. This crude peptide was then extracted with 1N acetic acid and filtered through a glass filter to remove the insoluble substances and resin, the filtrate being lyophilized. The dry product thus obtained was dissolved in a small amount of 1N acetic acid and applied to a column (2.7×90 cm) of Sephadex G-25 (Pharmacia). After elution with 1N acetic acid while monitoring absorbance at 280 nm or 254 nm, the fraction containing the desired peptide was collected and lyophilized.

To the chain A peptide containing non-protected cysteine residues was added dilute aqueous ammonia (pH 7.6) in a ratio of 1000 to 1 of peptide by volume; the mixture was kept standing at room temperature for 48 hours to form disulfide bonds, followed by lyophilization.

Each of the thus-obtained dry products of chains A and B was dissolved in 1N acetic acid and subjected to gradient elution with an acetonitrile-water system containing 0.1% TFA by reverse phase preparative HPLC (column: TSK gel ODS-120T, 2.15×30 cm). The peaks of the desired peptide were collected and lyophilized to yield a white powder. The purities of these peptides were determined by reverse phase HPLC. That they were the desired peaks was confirmed by the results of amino acid analysis following hydrolysis with 6N hydrochloric acid.

After the Acm groups were removed by iodine oxidation, chains A and B were each added to a column (2.7×90 cm) of Sephadex G-25, followed by elution with 1N acetic acid and lyophilization. Chains A and B corresponding to F007 were kept standing at room temperature in dilute aqueous ammonia (pH 7.6) for 24 hours to form disulfide bonds between chains A and B.

After confirmation of the progress of reaction by reverse phase HPLC, gradient elution with an acetonitrile-water system containing 0.1% TFA was conducted by reverse phase preparative HPLC on TSK gel ODS-120T (2.15×30 cm), and the desired fraction containing F007 was collected and lyophilized.

The thus-obtained peptide was identified as the desired peptide i.e. F007 by reverse phase HPLC and amino acid analysis. At the same time, the purity of the peptide was determined by the same analysis.

Example 5: Synthesis of F001

F001 was synthesized in the same manner as in Example 4, except that the cysteine residues protected by Acm were at the 7-position in chain A and the 7-position in chain B.

Example 6: Receptor Affinity (2) of Insulin Fragments

As directed in Example 3, the affinities of the insulin fragments (F007 and F001 respectively obtained in Examples 4 and 5 for the insulin receptor on the capillary endothelial cell were determined. They shows same affinity as insuline frogments obtained in Example 1 and 2.

Example 7: Blood Sugar Reducing Effect of Insulin Fragment

The blood sugar reducing effect of F007, in subcutaneous administration in the form of a solution in physiological saline to ICR mice, was rated in comparison with the bioactivity of insulin by the method described in Reference Example 1. The result is shown in Table 3. As shown in Table 3, 1 hour after administration, the blood sugar level was not significantly lower than that with insulin, when compared at the same dose. Even at a 10-fold dose, no extreme blood sugar reduction as with insulin was seen. This means that the insulin fragment F007 is less active than insulin in blood sugar reduction and possesses cerebral transport activity alone, demonstrating its utility as a carrier peptide.

TABLE 3

Blood Sugar Reducing Effect of F007

| Sample Given to ICR Mice | Blood Sugar Level (mg/dl) (n = 5) | | | | | Mean ± SE |
|---|---|---|---|---|---|---|
| Physiological saline | 291 | 222 | 175 | 223 | 241 | 230 ± 19 |
| Insulin (30 μg) | 113 | 116 | 101 | 108 | 121 | 112 ± 3 |
| F007 (30 μg) | 190 | 263 | 211 | 218 | 199 | 216 ± 13 |
| F007 (300 μg) | 166 | 203 | 158 | 161 | 161 | 170 ± 8 |

Example 8: Interleukin 2 (IL-2)-Carrier Peptide Conjugate 7 mg of F007 was dissolved in 1 ml of 0.1M phosphate buffer (pH 7.4). To this solution was added drop by drop a separately prepared SPDP/dimethylsulfoxide (DMSO) solution (7 mg/40 μl) while ice cooling; the mixture was then kept standing at room temperature for 30 minutes. This product was eluted with 0.1M phosphate buffer (pH 7.4) through a gel column PD-10 (Pharmacia), to remove the unreacted SPDP, and collected. Separately, 10 mg of recombinant human IL-2 (Takeda Chemical) was dissolved in 1 ml of 0.1M phosphate buffer (pH 7.4). To this solution was added drop by drop a separately prepared SPDP/DMSO solution (7 mg/40 μl) while ice cooling; the mixture was then kept standing at room temperature for 30 minutes. This product was eluted with 0.1M phosphate buffer (pH 7.4) through PD-10, to remove the unreacted SPDP, and collected. After buffer replacement with 0.1M sodium acetate solution (pH 4.5) using PD-10, the eluate was concentrated to 2.0 ml under reduced pressure and then reduced in the presence of 3.6% dithiothreitol in 0.1M sodium acetate solution (pH 4.5) at room temperature for 30 minutes. After elution with 0.1M phosphate buffer (pH 7.4) using PD-10 to remove small molecules, the eluate was collected. Next, SPDP-bound F007 and IL-2 were combined and kept standing for 18 hours; the resulting reaction broth was separated and purified through a column of Sephadex G-75 (Pharmacia). The structural formula of the thus-obtained F007-IL-2 is given below.

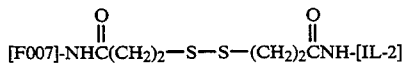

Example 9: $^{125}$I-Labeled Nerve Growth Factor (NGF)-Carrier Peptide Conjugate Recombinant human NGF as obtained by the method described in Japanese Unexamined Patent Publication No. 128300/1992 was first labeled with $^{125}$I by the chloramine T method. This was bound with F007 by means of SPDP as directed in Example 5; the resulting conjugate was then separated and purified by reverse phase HPLC, dialyzed against water and lyophilized to yield a conjugate ($^{125}$I-NGF-F007).

Example 10: Somatostatin-Carrier Peptide Conjugate

A somatostatin-F007 conjugate was obtained in the same manner as in Example 8, except that IL-2 was replaced with somatostatin.

Example 11: Vasopressin-Carrier Peptide Conjugate

A vasopressin-F007 conjugate was obtained in the same manner as in Example 8, except that IL-2 was replaced with vasopressin.

Example 12: Interferon α-Carrier Peptide Conjugate

An interferon α-F007 conjugate was obtained in the same manner as in Example 8, except that IL-2 was replaced with interferon α.

Example 13: bFGF-Carrier Peptide Conjugate

A bFGF-F007 conjugate was obtained in the same manner as in Example 8, except that IL-2 was replaced with bFGF.

Example 14: HRP-Carrier Peptide Conjugate

A HRP-F007 conjugate was obtained in the same manner as in Example 8, except that IL-2 was replaced with HRP.

Preparation Example

As a therapeutic agent for cerebral disease, the peptide conjugate of the present invention can be administered in the form of the following preparations:

1. 200 mg of the somatostatin-F007 conjugate obtained in Example 10 is dissolved in 10 ml of physiological saline and placed in a sprayer for an intranasally administrable preparation.

2. 10 mg of the vasopressin-F007 conjugate obtained in Example 11 is dissolved in 10 ml of physiological saline, and 100 mg of methyl cellulose is added to yield a viscous liquid for an intranasally administrable preparation.

3. 10 mg of the interferon α-F007 conjugate obtained in Example 12 is dissolved in 10 ml of physiological saline and prepared as an injectable solution for intravenous, subcutaneous and intramuscular administration by a conventional method.

4. 10 mg of the bFGF-F007 conjugate obtained in Example 13 is dissolved in 10 ml of physiological saline and prepared as an injectable solution for intravenous, subcutaneous and intramuscular administration by a conventional method.

---

What is claimed is:

1. A peptide conjugate capable of passing the blood-brain barrier, comprising a bioactive peptide or protein incapable of passing the blood-brain barrier and an insulin fragment consisting essentially of:
   (a) a peptide chain having 14 to 21 amino acid residues from the N-terminus of insulin chain A and
   (b) another peptide chain having 16 to 22 amino acid residues from the N-terminus of insulin chain B.

2. The conjugate as claimed in claim 1, wherein said insulin fragment is the fragment shown in FIG. 3 (residues 1–14 of SEQ ID NO: 1 and residues 1–16 of SEQ ID NO:2).

3. The conjugate as claimed in claim 1, wherein said insulin fragment is the fragment shown in FIG. 6(SEQ ID NOS 1 and 2).

4. The conjugate as claimed in claim 1, wherein said bioactive peptide or protein is a nerve nutrition factor.

5. The conjugate as claimed in claim 1, wherein said bioactive peptide is a neuropeptide.

6. The conjugate as claimed in claim 1, wherein said bioactive peptide or protein has a molecular weight in a range of about 200 dalton to about 120,000 daltons.

7. The conjugate as claimed in claim 1, wherein said bioactive peptide or protein has a molecular weight of about 400 to about 80,000 daltons.

8. The conjugate as claimed in claim 1, wherein said bioactive peptide or protein has a molecular weight of about 500 to about 60,000 daltons.

9. The conjugate as claimed in claim 1, wherein said insulin fragment has an internal disulfide crosslinkage between the 6th and 11th positions from the N-terminus of insulin chain A and two disulfide crosslinkages between chain A and chain B.

10. The conjugate as claimed in claim 1, which is a conjugate of the insulin fragment shown in FIG. 6 (SEQ ID NOS 1 and 2) with interleukin 2, somatostatin, vasopressin, interferon α, basic fibroblast growth factor or horseradish peroxidase.

* * * * *